United States Patent
Lin et al.

(10) Patent No.: US 8,814,805 B2
(45) Date of Patent: Aug. 26, 2014

(54) COMPLEX SIGNAL DEMODULATION AND ANGULAR DEMODULATION FOR NON-CONTACT VITAL SIGN DETECTION

(75) Inventors: Jenshan Lin, Gainesville, FL (US); Changzhi Li, Lubbock, TX (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 388 days.

(21) Appl. No.: 12/743,103

(22) PCT Filed: Dec. 8, 2008

(86) PCT No.: PCT/US2008/085899
§ 371 (c)(1),
(2), (4) Date: May 14, 2010

(87) PCT Pub. No.: WO2009/076298
PCT Pub. Date: Jun. 18, 2009

(65) Prior Publication Data
US 2010/0241010 A1    Sep. 23, 2010

Related U.S. Application Data

(60) Provisional application No. 61/005,782, filed on Dec. 7, 2007.

(51) Int. Cl.
*A61B 5/08* (2006.01)
*G01F 17/00* (2006.01)
*G01F 23/00* (2006.01)

(52) U.S. Cl.
USPC .............................. 600/534; 702/56

(58) Field of Classification Search
USPC ................. 600/529–543; 702/56
See application file for complete search history.

(56) References Cited

U.S. PATENT DOCUMENTS 5,694,093 A * 12/1997 DaSilva et al. ............. 332/103
7,073,384 B1 * 7/2006 Donskoy et al. ............ 73/657

(Continued)

FOREIGN PATENT DOCUMENTS

| JP | 2006-055504 | 3/2006 |
|---|---|---|
| WO | WO-2007-010460 | 1/2007 |
| WO | WO 2009/009722 | 1/2009 |

OTHER PUBLICATIONS

Li et al. "Experiment and Spectral Analysis of a Low-Power Ka-Band Heartbeat Detector Measuring From Four Sides of a Human Body." IEEE Transactions on Microwave Theory and Techniques. vol. 54, No. 12. Dec. 4, 2006.*

(Continued)

*Primary Examiner* — Michael D'Angelo
*Assistant Examiner* — Tiffany Weston
(74) *Attorney, Agent, or Firm* — Saliwanchik, Lloyd & Eisenschenk

(57) ABSTRACT

Methods for recovering a detected signal in non-contact vital sign detection are provided. According to one embodiment, a detected reflected signal from a non-contact vital sign detection system can be received and provided along I channel and Q channel signal lines. A complex signal S(t) can then be reconstructed from the I channel and Q channel signal lines through complex signal demodulation. A Fourier transform can be used to obtain the detected signal's spectrum for spectrum analysis. Angular demodulation can be used to recover the information corresponding to original body movement. The complex signal demodulation and angular demodulation techniques used to provide information to determine original body movement are capable of avoiding the null detection point without limitations on frequency tuning or channel selection.

31 Claims, 9 Drawing Sheets

(56) References Cited

U.S. PATENT DOCUMENTS

| | | |
|---|---|---|
| 2002/0007119 A1 | 1/2002 | Pelissier |
| 2004/0039282 A1 | 2/2004 | Szabo et al. |
| 2004/0181143 A1 | 9/2004 | Israel |
| 2005/0128123 A1 | 6/2005 | Greneker, III et al. |
| 2006/0209631 A1* | 9/2006 | Melese et al. .................... 367/7 |
| 2007/0265531 A1 | 11/2007 | He et al. |
| 2008/0269589 A1 | 10/2008 | Thijs et al. |
| 2010/0130873 A1 | 5/2010 | Yuen et al. |
| 2010/0158331 A1 | 6/2010 | Jacobs et al. |
| 2010/0179438 A1 | 7/2010 | Heneghan et al. |
| 2010/0198083 A1 | 8/2010 | Lin et al. |
| 2010/0204587 A1 | 8/2010 | Lin et al. |
| 2010/0241010 A1 | 9/2010 | Lin et al. |

OTHER PUBLICATIONS

Droitcour, Amy. "Non-Contact Measurement of Heart and Respiration Rates with a Single Chip Microwave Doppler Radar." Jun. 2006. Standford University.*

Li, C., et al., "Complex Signal Demodulation and Random Body Movement Cancellation Techniques for Non-Contact Vital Sign Detection," *Microwave Symposium Digest*, 2008 IEEE MTT-S International, 2008, pp. 567-570.

Li, C., et al., "Experiment and Spectral Analysis of a Low-Power Ka-Band Heartbeat Detector Measuring From Four Sides of a Human Body," *IEEE Transactions on Microwave Theory and Techniques*, Dec. 2006, pp. 4464-4471, vol. 54, No. 12.

Li, C., of al., "Random Body Movement Cancellation in Doppler Radar Vital Sign Detection," *IEEE Transactions on Microwave Theory and Techniques*, Dec. 2008, pp. 3143-3152, vol. 56, No. 12.

Budge, Jr., M.C., et al., "Range Correlation Effects on Phase and Amplitude Noise", *Proc. IEEE Southeast Conf.*, 1993, pp. 5-9.

Droitcour, A.D., et al., "Range Correlation and I/Q Performance Benefits in Single-Chip Silicon Doppler Radars for Non-contact Cardiopulmonary Monitoring," *IEEE Trans. Microwave Theory and Techniques*, Mar. 2004, pp. 838-848, vol. 52, No. 3.

Li, C., et al., "Complex Signal Demodulation and Random Body Movement Cancellation Techniques for Non-Contact Vital Sign Detection", *Microwave Symposium Digest, IEEE MTT-S International*, Jun. 2008, pp. 567-570.

Li, C., etal., "Design Guidelines for Radio Frequency Non-Contact Vital Sign Detection," *Proceedings of the 29$^{th}$ Annual International Conference of the IEEE EMBS*, Aug. 2007, pp. 1651-1654.

Li, C., et al., "Optimal Carrier Frequency of Non-Contact Vital Sign Detectors," *Proceedings of IEEE Radio and Wireless Symposium*, Jan. 2007, pp. 281-284.

Park, B., et al., "Arctangent Demodulation with DC Offset Compensation in Quadrature Doppler Radar Receiver Systems", *IEEE Trans. Microwave Theory and Techniques*, May 2007, pp. 1073-1079, vol. 55, No. 5.

Office Action dated May 10, 2013 in U.S. Appl. No. 12/668,700.

Notice of Allowance dated Dec. 24, 2013 in U.S. Appl. No. 12/668,700.

* cited by examiner

COMPLEX SIGNAL DEMODULATION AND ANGULAR DEMODULATION FOR NON-CONTACT VITAL SIGN DETECTION

CROSS-REFERENCE TO RELATED APPLICATIONS

The present application is the U.S. National Stage Application of International Patent Application No. PCT/US2008/085899, filed on Dec. 8, 2008, which claims the benefit of U.S. Provisional Application Ser. No. 61/005,782, filed Dec. 7, 2007, both of which are hereby incorporated by reference herein in their entirety, including any figures, tables, or drawings.

BACKGROUND OF INVENTION

Radar techniques can be used to detect minute body movements, including movements associated with cardiac and respiratory activity, body tremors, and gait signature. Functionally, a non-invasive, electromagnetically-based vital signs detection system is an extremely sensitive motion detection system capable of detecting small body motions. Motion detection is achieved by transmitting an interrogating electromagnetic field at the target of interest, and then measuring the time-delay of the return signal reflected back from the surface of the target. When the target surface is moving, as does the surface of the chest in conjunction with respiratory and cardiac activities, corresponding variations will be observed in the measured time delay. The observed variations can be used to determine motion-related target parameters such as displacement and velocity.

An electromagnetically-based vital signs detection system can easily be used in a completely non-contacting mode and can be placed an appreciable distance from the test subject. Electromagnetic signals in the microwave band are also capable of penetrating through heavy clothing and walls.

Applications can include heart and respiration monitoring, heart disease screening, finding persons behind walls and in closed areas, and deception detection (lie detector) using heart and respiration channels of polygraph.

In operation of a vital signs detection system, a beam of radio frequency energy is directed towards the body of a subject. The reflected signal contains phase information representing the movement of the surface of the body, from which respiration and heartbeat information can be obtained. The reflected phase modulated energy is typically received and demodulated by the detection system using synchronous quadrature detection. The quadrature signals so obtained can then be signal processed to obtain the heartbeat and respiratory information of interest. Analysis of the vital signs waveform can be used for estimation of, for example, cardiac function and blood pressure.

One problem in sensing the movement of the surface of a subject is the occurrence of periodic nulls in the sensing field. Thus, it is possible to fail to detect motion from a subject depending on the subject's range from the transceiver. This problem is referred to as a null detection point problem. In a typical technique, two quadrature channels are compared, and then the result from the channel with better performance (i.e., the result closer to the optimal detection point) is used. However, the channel having better performance is dependent on the distance between the transceiver and the subject, which changes from case to case in real applications.

Another technique to avoid a null detection point is using double-sideband transmission and frequency tuning. However, this technique requires tuning the intermediate frequency as the subject-to-antenna distance changes.

A further challenge for non-contact vital sign detection is the noise caused by random body movement, which presents severe interference for accurate detection of respiration and heartbeat signal in practical applications. Since random body movement is comparable or even stronger than certain weak vital sign signals, it has been difficult to implement non-contact vital sensors.

Accordingly, there exists a need in the art for improved detection accuracy of a vital signs waveform.

BRIEF SUMMARY

Embodiments of the present invention relate to a method and apparatus for recovering a detected signal in non-contact vital sign detection. Embodiments of the subject method and apparatus can also be applied to recover detected signals from other vibrating objects having vibrations at two or more frequencies.

Embodiments of the present invention provide complex signal demodulation and angular demodulation techniques capable of avoiding the null detection point without limitations on frequency tuning or channel selection.

Further embodiments of the present invention are capable of separating signals representing random body movement from those representing physiological movement for vital sign detection.

In one embodiment, a reflected signal from a non-contact vital sign detection system can be received and provided along I channel and Q channel signal lines. A complex signal $S(t)$ can then be reconstructed from the I channel and Q channel signal lines. This complex signal $S(t)$ can be transformed from the time domain to the frequency domain using, for example, a fast Fourier transform. The frequency domain transformed complex signal can be analyzed through spectrum analysis and its angular information can be used to determine original body movement.

In a further embodiment, a second transceiver portion can be used to provide a second complex signal $S_2(t)$ reconstructed from a second reflected signal received and provided along I channel and Q channel signal lines. The second complex signal can be multiplied with the first complex signal $S(t)$ to provide a combined complex signal $B(t)$. Then a spectral analysis can be conducted with respect to the combined complex signal $B(t)$. When the second transceiver portion is positioned in front of a subject, and the first transceiver is positioned in back of the subject, the combined signal can provide random body movement cancellation.

Embodiments of the present invention can be used in place of prior signal recovery techniques. Embodiments of the present invention can improve detection accuracy and provide robust final products.

BRIEF DESCRIPTION OF DRAWINGS

FIG. 3A shows a time domain signal of the I 2 and the Q 4 channel; FIG. 3B shows angular information obtained from the complex signal reconstructed from the I and the Q channel; FIG. 3C shows a baseband spectrum of the Q channel; FIG. 3D shows a baseband spectrum of the I channel; FIG. 3E shows a baseband spectrum of the angular information shown in FIG. 3B; and FIG. 3F shows a trajectory of angular demodulation.

FIG. 6A shows the spectrum detected from the front and the back of the subject as the body is moving randomly as shown in the inset, and FIG. 6B shows the spectrum recovered by the random body movement cancellation technique when DC offset is calibrated out, with the inset showing the heartbeat spectrum when DC offset/signal amplitude=0.2 (I), 0.4 (II), and 0.6 (III).

FIG. 9A shows a complex signal demodulated spectrum measured from the front and the back of the human body and FIG. 9B shows a combined spectrum by the random body movement cancellation technique, where the heartbeat information is successfully recovered.

DETAILED DISCLOSURE

Embodiments of the present invention relate to a method and apparatus for recovering a detected signal in non-contact vital sign detection. Embodiments of the subject method and apparatus can also be applied to recover detected signals from other vibrating objects having vibrations at two or more frequencies. Embodiments can include transmitting a signal at a target and receiving a reflected signal from the target, where the frequency of the signal is in the range of 9 kHz-1 terahertz, and in a further specific embodiment in the range of 1 GHz-30 GHz.

Embodiments of the present invention provide a complex (both real part and imaginary part) signal reconstruction technique for recovering a detected signal in non-contact vital sign detection. Such vitals sign can include respiration and heart beat. The subject methods can also be applied to detection of signals from other vibrating objects having vibrations at two or more frequencies. A received signal can be filtered using the subject methods to provide vital sign information in non-contact applications.

Advantageously, embodiments of the subject method can completely remove the null detection point problem without the need of frequency tuning, or the decision of optimal/null detection of the two quadrature channels.

In addition, embodiments of the present invention are robust against DC offset in a direct conversion system. This can be accomplished because DC offset of the two quadrature channels produce DC offset in the reconstructed complex signal without affecting the desired signal components. The DC offset in the complex signal can be removed in software by extracting the average from each time domain sliding window. In contrast other techniques used in a direct conversion system, such as arctangent demodulation and envelope detection, are very sensitive to DC offset.

Furthermore, in embodiments of the present invention, the DC offset of the system can be calibrated out such that the complex signal can be used to recover the angular information of the detected signal. The angular demodulation technique according to the present invention can inhibit the occurrence of the harmonic problem of non-contact vital sign detection. In fact, there is no non-linear harmonic effect by analyzing the angular information of detected signal according to an embodiment of the present invention.

Further embodiments of the present invention are capable of separating signals representing random body movement from those representing physiological movement for vital sign detection.

Figure 1A:
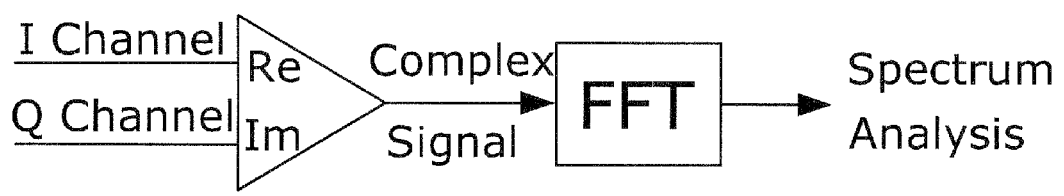
FIGS. 1A-1B show a block diagram for a complex signal demodulation process (FIG. 1A) and an angular demodulation process (FIG. 1B) according to an embodiment of the present invention.
Figure 1B:
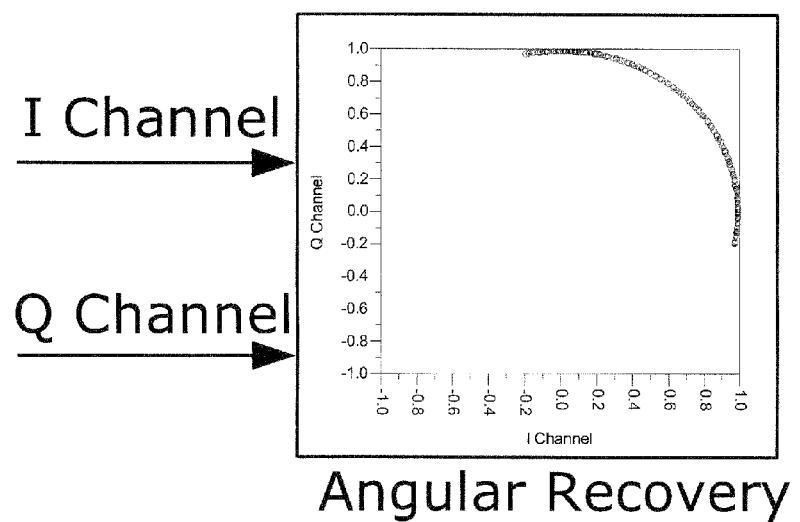

Referring to FIG. 1A, for complex signal demodulation, a real in-phase component of the received signal, which is in phase with the transmitted wave, and an imaginary quadrature component Q of the received signal, which is 90 degrees out of phase with the transmitted wave are reconstructed as the complex signal S(t). Then, a Fourier transform is applied to the signal S(t) to obtain the detected spectrum for spectrum analysis. During spectrum analysis, angular recovery of the detected signal can be obtained. FIG. 1B shows the result of extracted angular information of the complex signal S(t), which provides the spectrum of the phase.

For non-contact quadrature demodulation of vital signs, the signals detected by the I and the Q channels can be obtained by spectral analysis:

$$I(t) = \cos\left(\frac{4\pi x_h(t)}{\lambda(\text{eq.1b})} + \frac{4\pi x_r(t)}{\lambda} + \phi\right) \quad \text{Equation 1a}$$

$$= \sum_{k=-\infty}^{\infty} \sum_{l=-\infty}^{\infty} J_k\left(\frac{4\pi m_r}{\lambda}\right) J_l\left(\frac{4\pi m_h}{\lambda}\right) \cos(k\omega_r t + l\omega_h t + \phi)$$

$$= DC_I - 2[C_{10}\sin(\omega_r t) + C_{01}\sin(\omega_h t) + \dots] \cdot$$
$$\sin\phi + 2[C_{20}\cos(2\omega_r t) + C_{02}\cos(2\omega_h t) + \dots] \cdot \cos\phi$$

(result used as eq.1b for above)

$$Q(t) = \sin\left(\frac{4\pi x_h(t)}{\lambda} + \frac{4\pi x_r(t)}{\lambda} + \phi\right) \quad \text{Equation 1b}$$

$$= \sum_{k=-\infty}^{\infty} \sum_{l=-\infty}^{\infty} J_k\left(\frac{4\pi m_r}{\lambda}\right) J_l\left(\frac{4\pi m_h}{\lambda}\right) \sin(k\omega_r t + l\omega_h t + \phi)$$

$$= DC_Q + 2[C_{10}\sin(\omega_r t) + C_{01}\sin(\omega_h t) + \dots] \cdot$$
$$\cos\phi + 2[C_{20}\cos(2\omega_r t) + C_{02}\cos(2\omega_h t) + \dots] \cdot \sin\phi$$

where $x_h(t)=m_h \sin(\omega_h t)$ and $x_r(t)=m_r \sin(\omega_r t)$ are periodic body movements due to respiration and heartbeat, $J_n$ is the Bessel function of the first kind, $\lambda$ is the wavelength of wireless signal, $\phi$ is the total residual phase accumulated in the circuit and along the transmission path.

$$C_{ij} = J_i\left(\frac{4\pi m_r}{\lambda}\right) J_j\left(\frac{4\pi m_h}{\lambda}\right)$$

determines the amplitude of every frequency component, $$DC_I = J_0\left(\frac{4\pi m_r}{\lambda}\right) \cdot J_0\left(\frac{4\pi m_h}{\lambda}\right) \cdot \cos\phi \text{ and}$$

$$DC_Q = J_0\left(\frac{4\pi m_r}{\lambda}\right) \cdot J_0\left(\frac{4\pi m_h}{\lambda}\right) \cdot \sin\phi$$

are the DC components of the signals in I and Q channels, respectively. The ellipses in equations 1a and 1b represent higher order odd and even harmonies. The $DC_I$ and $DC_Q$ terms are the DC information directly related to the physiological movement, and can be useful for recovering the vital sign signals in certain situations. In specific embodiments, the measured baseband level is the $DC_I/DC_Q$ level plus an "undesired DC offset", due to the DC offset caused by the signals reflected from environmental stationary objects (clutter) and the DC offset accumulated in the electronic circuit.

Figure 2A:
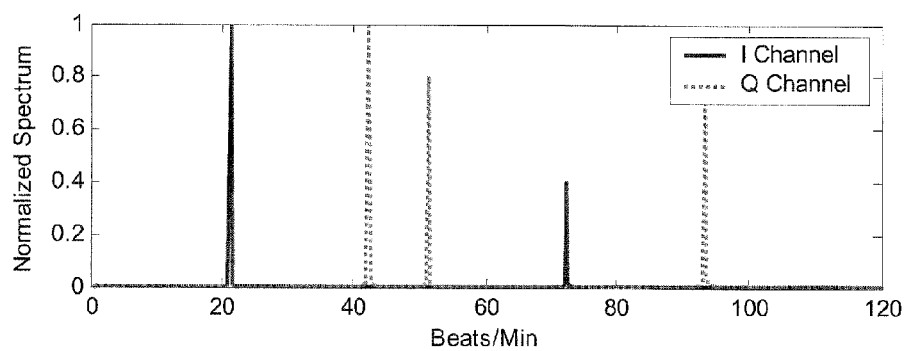
FIGS. 2A-2B show a normalized spectrum of the I and Q channels separately (FIG. 2A) and combined (FIG. 2B), according to an embodiment of the present invention.

From Equations (1a) and (1b), the ratio of $\cos\phi$ and $\sin\phi$ in each channel determines the relative strength between even order and odd order harmonics. Therefore, the optimal/null detection point is determined by the residue phase $\phi$. For example, when $\phi$ is close to 90°, the fundamental frequency of respiration and heartbeat signals dominate in the I channel while the second order harmonic of desired signals dominate in the Q channel, thus I is close to optimal detection point and Q is close to null detection point. This is shown in FIG. 2A, which shows spectra of the I and Q channels. Therefore, when one of the two quadrature channels is close to an optimal detection point, the other channel should be close to the null detection point. For FIG. 2A, it is undetermined which channel is at the optimal/null detection point.

Figure 2B:
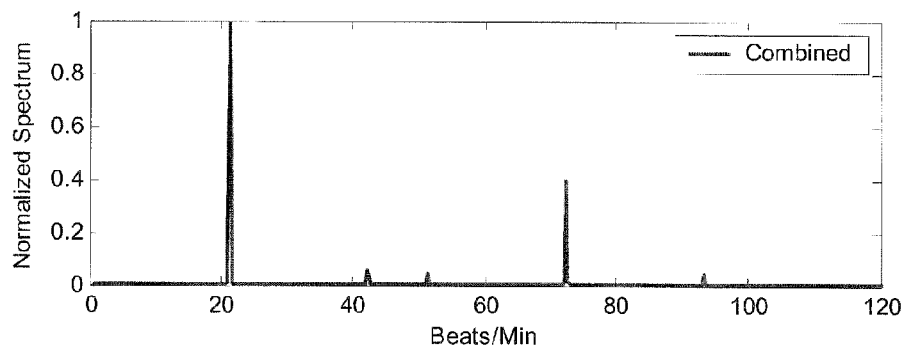
Figure 3A:
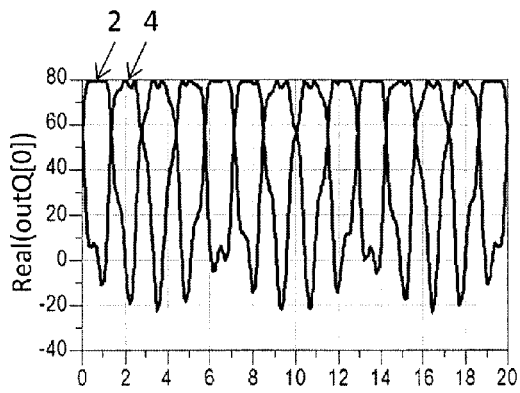
FIGS. 3A-3F show time and frequency domain plots along steps of an angular demodulation process according to an embodiment of the present invention, where
Figure 3B:
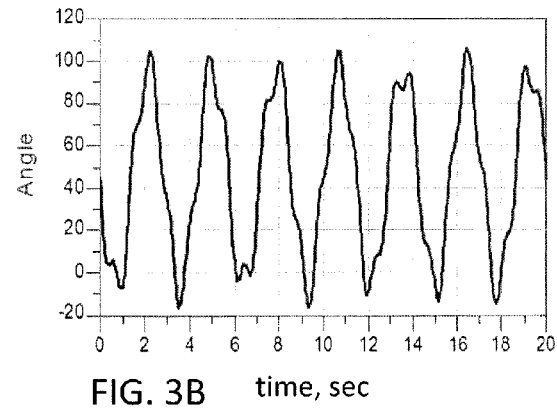
Figure 3C:
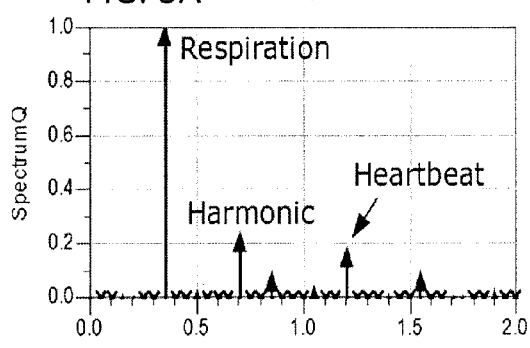
Figure 3D:
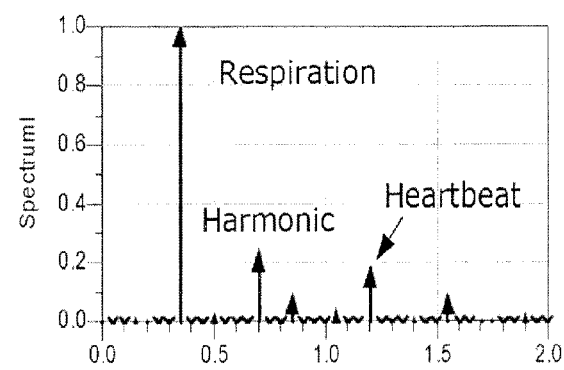
Figure 3E:
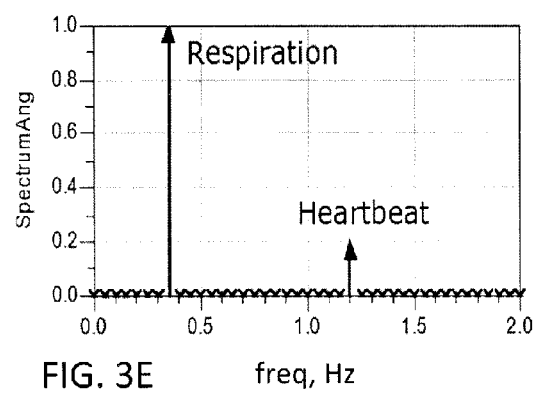
Figure 3F:
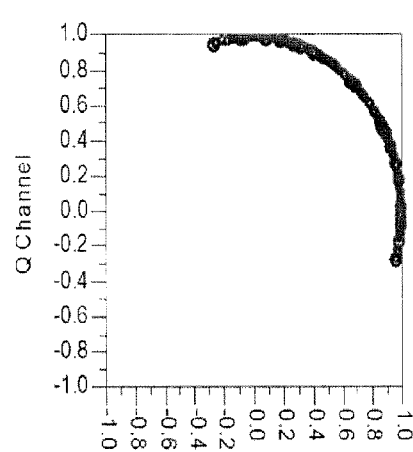

In the complex signal demodulation method as shown in FIG. 1A, the complex signal can be reconstructed in software by:

$$S(t) = I(t) + j \cdot Q(t) \qquad \text{Equation 2}$$

$$= e^{j\left[\frac{4\pi x_h(t)}{\lambda} + \frac{4\pi x_r(t)}{\lambda} + \varphi\right]}$$

$$= DC_{IQ} + 2j[C_{10}\sin(\omega_r t) + C_{01}\sin(\omega_h t) + \dots] \cdot e^{j\varphi} +$$

$$2j[C_{20}\cos(2\omega_r t) + C_{02}\cos(2\omega_h t) + \dots] \cdot e^{j\varphi}$$

where $DC_{IQ} = DC_1 + j \cdot DC_Q$. When a complex Fourier transform is applied to the signal S(t) to obtain the detected spectrum, the residual phase $\phi$ will not affect the relative strength between the odd order and the even order frequency components, since the amplitude of $e^{j\Phi}$ is always one. Therefore, desired signal components (odd order tones) will always be present in the spectrum. This can be seen in FIG. 2B, which shows a spectrum obtained by complex signal demodulation according to an embodiment of the present invention. According to such an embodiment, the null detection case can be avoided.

The DC components accumulated in the I and the Q channels only contribute to the DC term in the reconstructed signal S(t). The DC term in the reconstructed signal S(t) can be removed from the detected spectrum without affecting desired signal components by subtracting the complex average from every time domain sliding window.

Therefore, by calibrating out the DC offset of the system, the angular information of the complex signal can be extracted as:

$$\text{Phase}[S(t)] = \frac{4\pi x_h(t)}{\lambda} + \frac{4\pi x_h(t)}{\lambda} + \phi \qquad \text{Equation 3}$$

In this way, the effect of a non-linear transfer function can be eliminated, such that there will be no harmonics of the desired signal component or intermodulation between the desired signal components. The spectrum of the phase, which is the angular information of the detected signal, only has the information of real body movement.

Accordingly, embodiments of the present invention can obtain original body movement information by recovering the angular information from the complex signal. This technology, where original body movement information can be obtained by recovering angular information from a reconstructed complex signal, can be referred to as angular demodulation.

FIG. 3 shows an example of angular demodulation when both the I and the Q channel are at the point between the optimal and the mill detection point. FIG. 3A shows time domain signals of the I 2 and the Q 4 channels; FIG. 3B shows angular information obtained from the complex signal reconstructed from the I and the Q channels; FIG. 3C shows a baseband spectrum of the Q channel; FIG. 3D shows a baseband spectrum of the I channel; FIG. 3E shows a baseband spectrum of the angular information shown in FIG. 3B; and FIG. 3F shows a trajectory of angular demodulation. In the specific embodiment illustrated in FIGS. 3A-3F, where both the I and the Q channels are at a point between the optimal and the null, the baseband spectrum of the I and the Q channel (FIG. 3C and FIG. 3D) are the same, with second harmonic of respiration signal presenting as an interference for accurate detection. The angular information of the detected signal is obtained from the complex combination of the two channels, as shown in FIG. 3B. It is shown clearly in FIG. 3E that undesired harmonics are removed from the baseband spectrum. In fact, neither undesired harmonics nor intermodulation interference is present in FIG. 3E. FIG. 3F shows the trajectory of the complex signal, which can be also called a constellation diagram. The signal moves back and forth along the circle from one end to the other.

Figure 4A:
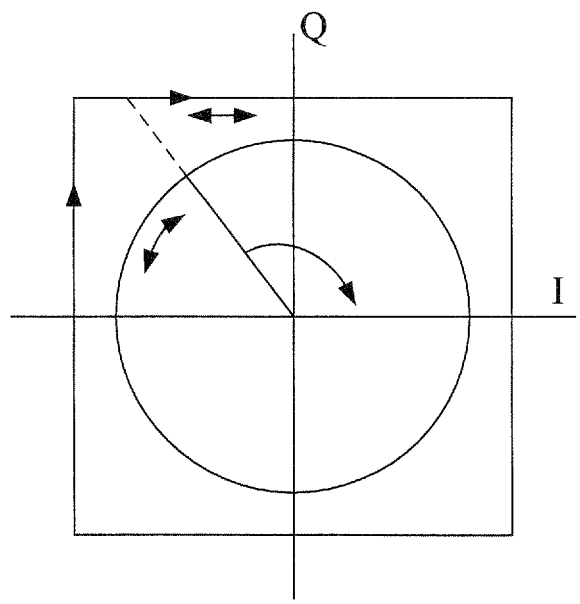
FIGS. 4A-4B show a plot of a trajectory of a received signal amplitude (angle vs. time) (FIG. 4A) and a plot of I and Q waveforms in time domain (FIG. 4B) according to an embodiment of the present invention.
Figure 4B:
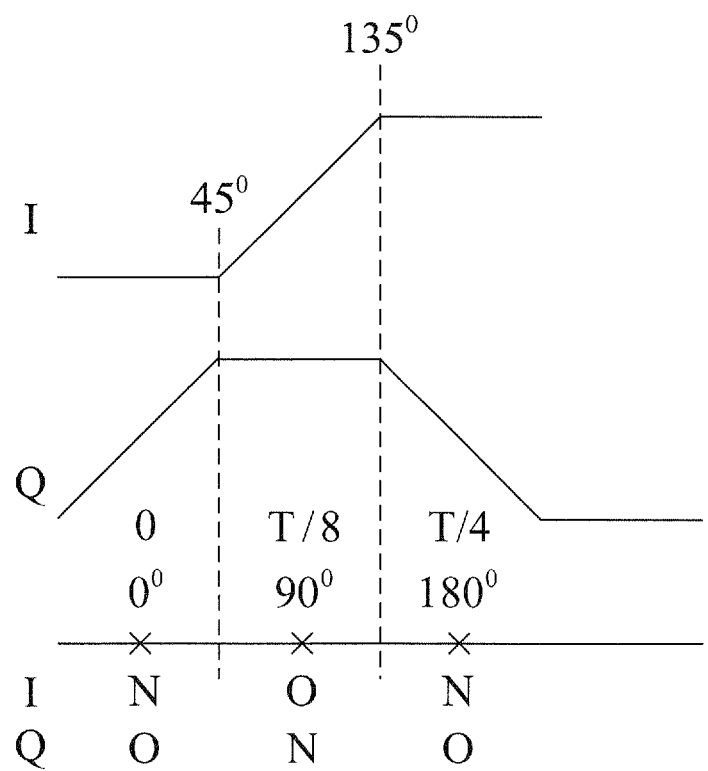

As shown in FIG. 4A, the angle vs. time (angular waveform) is still the same even if the received signal amplitude (radius of the trajectory) is very large and saturated (limited by the maximum voltage swing in either I or Q channel) as indicated by the square shape trajectory. In this saturated square trajectory, the I and Q waveforms in time domain are plotted in FIG. 4B, with the null detection points and optimum detection points in I and Q channels indicated. By using angular demodulation, the null point detection is no longer a problem. Furthermore, the harmonic distortion effect due to a nonlinear transfer function in either I or Q channel no longer exists. The movement of the subject moves the detected signal along the trajectory. If the subject moves fast, the signal on the trajectory moves fast too. This technique can also reveal the real harmonics of the movement itself.

In a further embodiment of the present invention, a method and apparatus are provided for reducing noise interference caused by random body movement. The random body movement cancellation technique (RBMCT) according to certain embodiments of the present invention uses multiple antennas and transceivers to detect from two sides, such as the front and the back, of the human body. By using polarization and frequency multiplexing, signals detected from different body orientations can be combined without interfering each other, and noise caused by random body movement can be cancelled out.

Because the chest wall movement caused by respiration and heartbeat is very small, random body movement can present a serious noise source for non-contact vital sign detection. Embodiments of the present invention can reduce or eliminate the noise from random body movement by recognizing the movement patterns.

Figure 5:
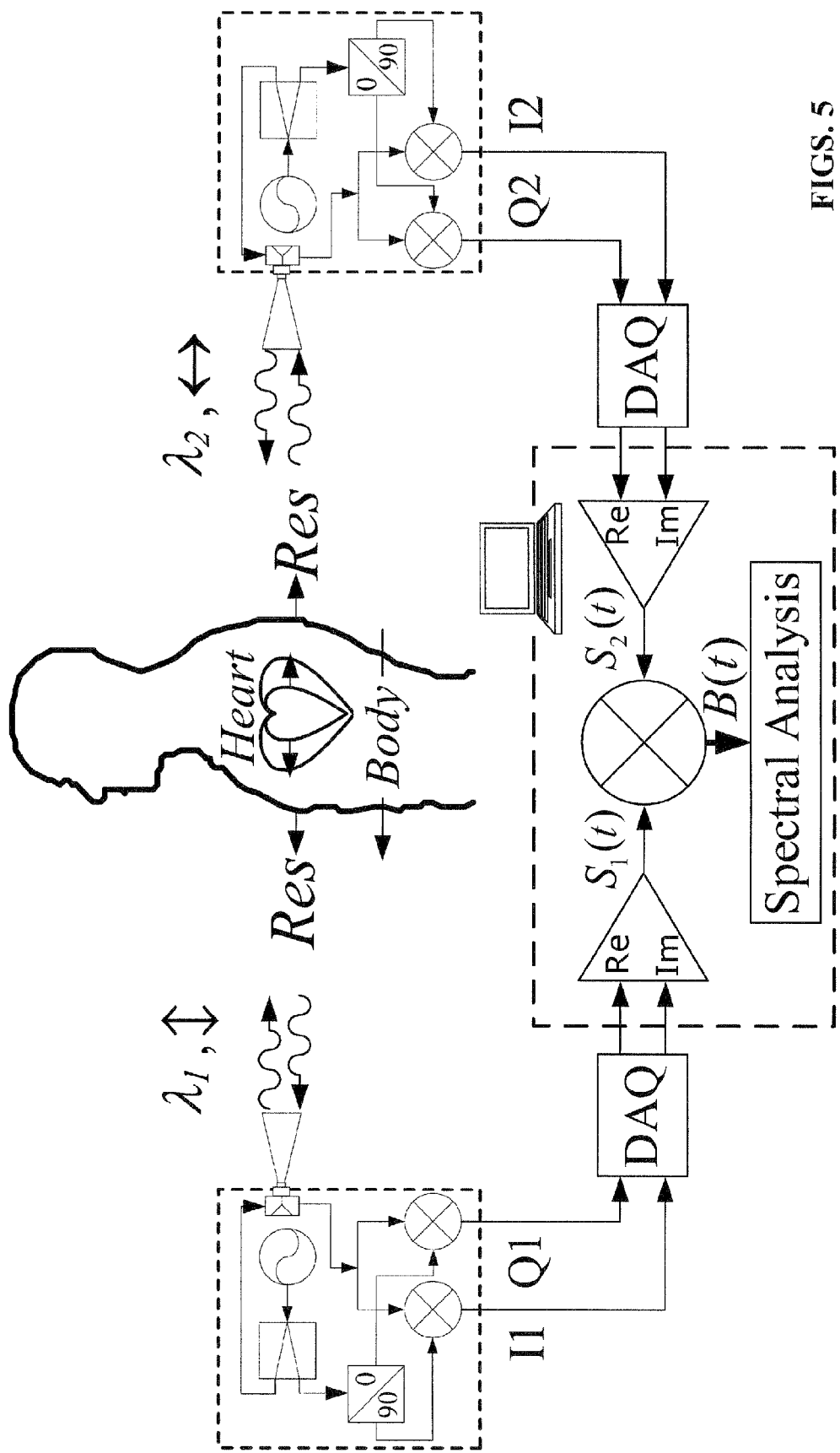
FIG. 5 shows a block diagram of a system setup for a random body movement cancellation technique according to an embodiment of the present invention.

FIG. 5 shows a block diagram for a random body movement cancellation technique and apparatus according to an embodiment of the present invention. A first transceiver is provided in front of a human body and a second transceiver is provided in back of the human body. The transceivers can each include an oscillator 10, power splitter 11, phase splitter 12, and multipliers 13. The transceiver block diagram is simplified and may include other components such as low noise amplifiers and high gain blocks, which are used in transceiver circuits for non-contact vital sign detection. The I channel and Q channel signals can pass through a data acquisition module (DAQ) before undergoing complex signal demodulation through reconstruction of the complex signals. The complex signal demodulation component and random body movement cancellation can be performed using a processor such as a computer running a software program.

As shown in FIG. 5, the two transceivers are transmitting and receiving signals with different polarization and wavelength. As the human body roams randomly in a certain direction (shown as the 'Body' arrow in FIG. 5), the heartbeat and the respiration cause the front and the back of the chest walls to move in the opposite directions. In the view of the two transceivers, the heartbeat-and-respiration-caused body movements are in phase, while the random body movements are out of phase. This means that when the subject is roaming toward one transceiver, it is moving away from the other transceiver.

Applying a complex signal demodulation technique according to an embodiment of the present invention, the signal detected from the two transceivers can be expressed as:

$$S_1(t) = \exp\left\{j\left[\frac{4\pi m_{r1}\sin(\omega_r t)}{\lambda_1} + \frac{4\pi m_{h1}\sin(\omega_h t)}{\lambda_1} - \frac{4\pi vt}{\lambda_1} + \phi_1\right]\right\} \quad \text{Equation 4}$$

$$S_2(t) = \exp\left\{j\left[\frac{4\pi m_{r2}\sin(\omega_r t)}{\lambda_2} + \frac{4\pi m_{h2}\sin(\omega_h t)}{\lambda_2} - \frac{4\pi vt}{\lambda_2} + \phi_2\right]\right\},$$

where v is a random variable representing the velocity of random body movement. The desired physiological signal presents a phase modulation in the baseband signal, while the random body movement presents a random frequency drift in the baseband signal. By multiplying the two complex signals, the output B (t) can be obtained as:

$$B(t) = S_1(t) \cdot S_2(t) \quad \text{Equation 5}$$

$$= \exp\left\{j\left[4\pi\left(\frac{m_{r1}}{\lambda_1} + \frac{m_{r2}}{\lambda_2}\right)\sin(\omega_r t) + 4\pi\left(\frac{m_{h1}}{\lambda_1} + \frac{m_{h2}}{\lambda_2}\right)\sin(\omega_h t) - \left(\frac{1}{\lambda_1} - \frac{1}{\lambda_2}\right)4\pi vt + \phi_1 + \phi_2\right]\right\}$$

$$\approx \exp\left\{j\left[\frac{4\pi(m_{r1}+m_{r2})}{\lambda}\sin(\omega_r t) + \frac{4\pi(m_{h1}+m_{h2})}{\lambda}\sin(\omega_h t) + \phi_1 + \phi_2\right]\right\},$$

where the approximation is valid for $\lambda_1$ and $\lambda_2$ chosen to be close to each other. In a specific embodiment, $\lambda_1$ and $\lambda_2$ are within 1% of each other, with 0.1% of each other, within 0.01% of each other, and within 0.0001% of each other. The operation in Equation 5 corresponds to convolution and frequency shift in the frequency domain, thus canceling the Doppler frequency drift and only keeping the periodic Doppler phase effects.

Figures 6A, 6B:
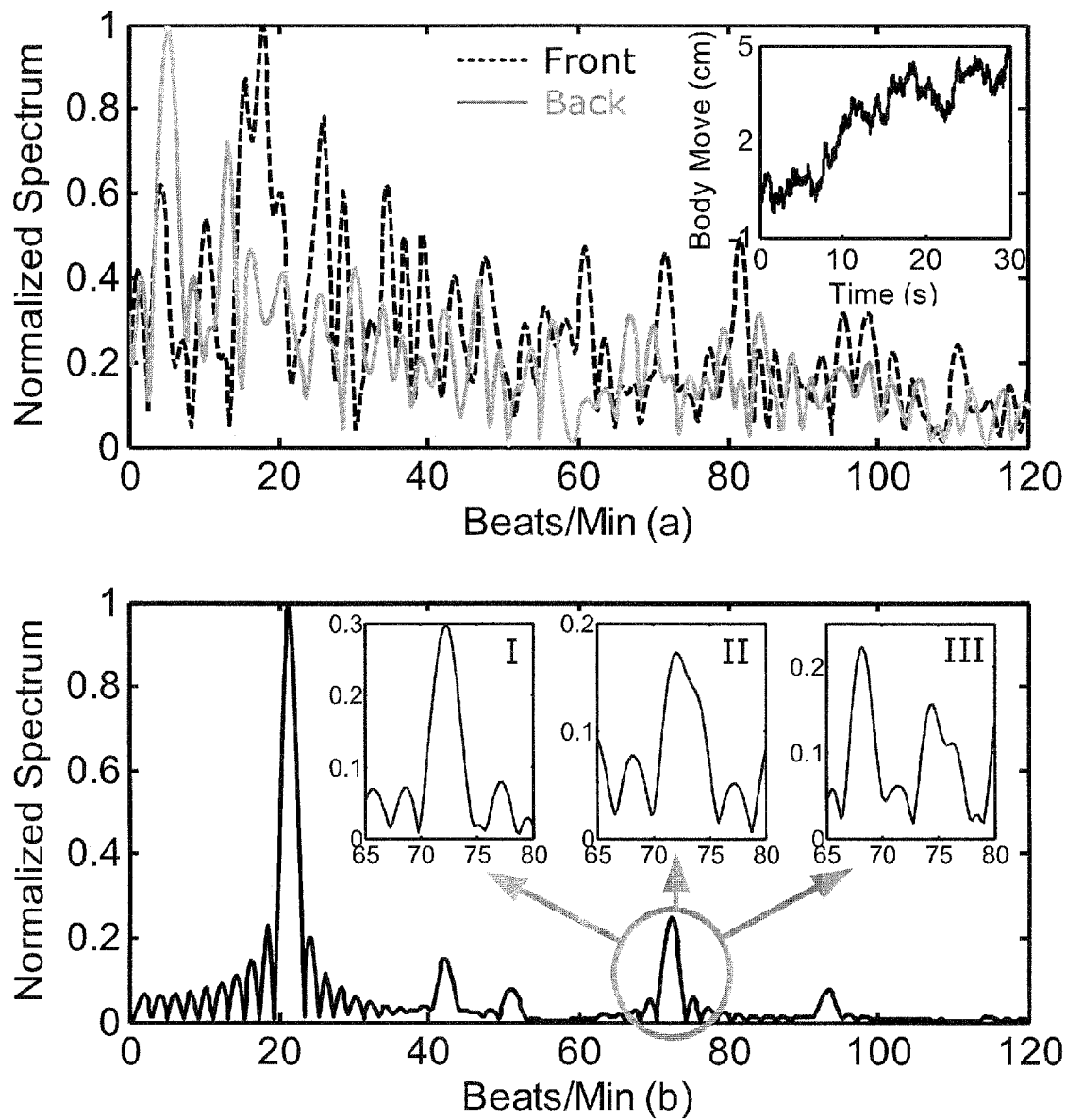
FIGS. 6A-6B show simulation results of a random body movement cancellation technique in accordance with an embodiment of the invention, where

Simulations have been performed to verify this technique. The time domain signals detected from the front and the back of the human body are generated from Equation 4, where the random body movement has a maximum of 5 cm displacement from the original body position as shown in the inset of FIG. 6A. The combined signal is obtained from Equation 5. FIGS. 6A-6B show the spectrum of the signal detected in each channel (FIG. 6A) and the spectrum of the combined signal (FIG. 6B). As illustrated by FIG. 6B, the random body movement can be removed from the combined signal, and a clear spectrum of desired signals can be obtained.

However, the random body movement cancellation technique is not immunized against DC offset. The inset of FIG. 6B shows the spectrum around the heartbeat frequency when DC offset is present in the system. As the amplitude of DC offset increases from 0.2 to 0.6 of the desired signal amplitude, more noise is added to the spectrum until the desired signal is completely overwhelmed by noise (inset III). The noise in the spectrum caused by DC offset in the system can be removed by performing a DC offset calibration. In one embodiment, the DC term can be removed from the detected spectrum without affecting desired signal components by subtracting the complex average from every time domain sliding window.

According to an embodiment of the present invention, in order to inhibit the signal from one unit of the two transceivers that are facing each other from saturating or interfering with the receiver link of the other of the two transceivers, polarization and frequency multiplexing can be utilized. In a specific embodiment, patch array antennas with orthogonal polarization pattern can be used for the two units. Free running voltage controlled oscillators (VCOs) can be used for the two transmitters so that $\lambda_1$ and $\lambda_2$ are close to each other but have a slight difference because the system does not incorporate any phase-locked-loop. Therefore, the signal from one transceiver can be rejected by the other transceiver in the baseband, because the small difference in the carrier frequency results in a large difference in baseband frequency for vital sign detection, which is typically no higher than several hertz.

Figure 7:
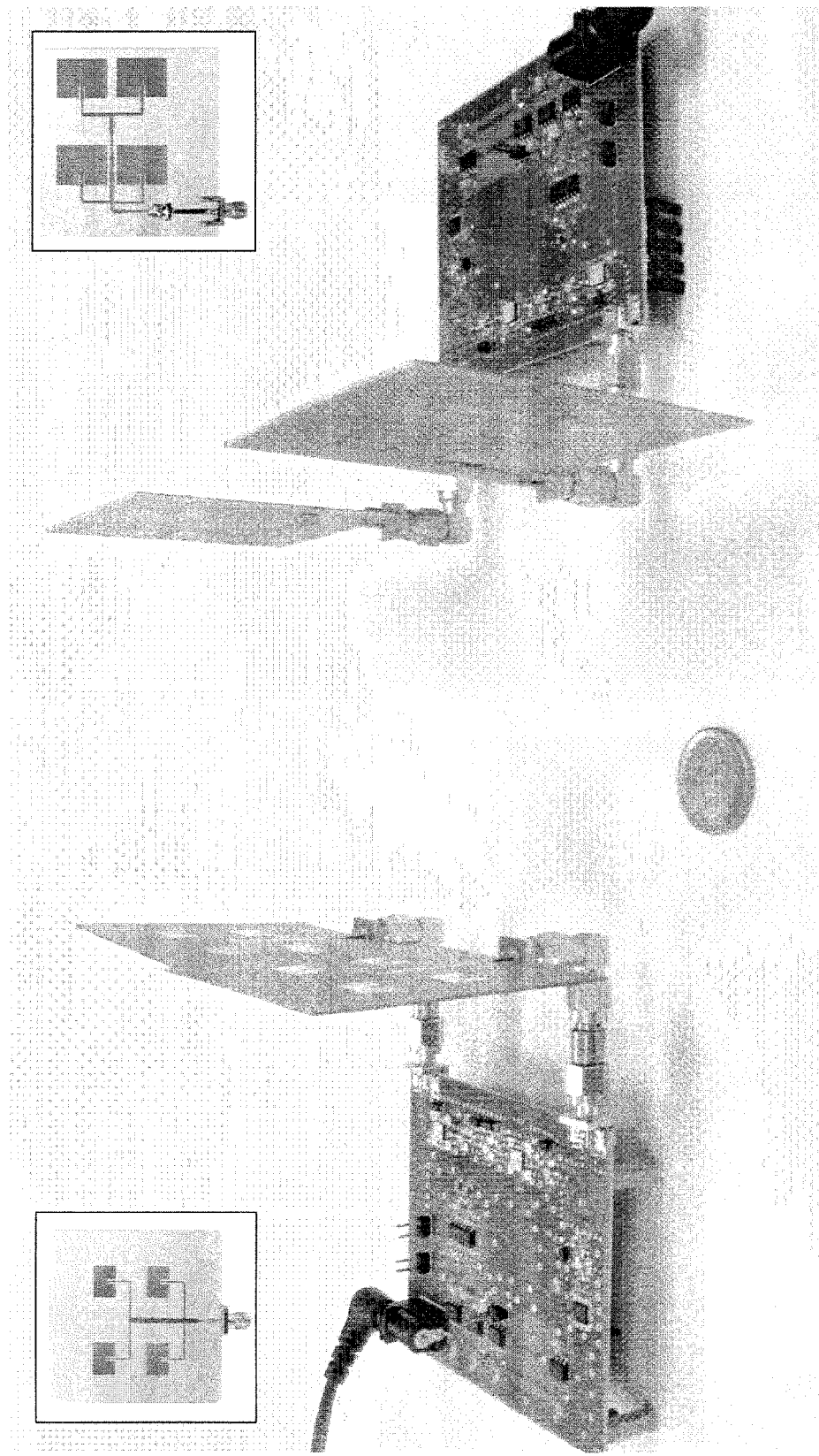
FIG. 7 shows two identical transceivers that can be used in accordance with an embodiment of the invention, with the insets showing the antenna used for each transceiver, where one transceiver uses a vertically polarized antenna array and the other transceiver uses a horizontally polarized antenna array.

Experimental Results:

Experiments were conducted using 5-6 GHz portable radars, which integrate a quadrature transceiver, a two-stage baseband amplifier, and a power management circuit on a single Rogers printed circuit board (RO4350B) with a size of 6.8 cm×7.5 cm. The amplified baseband output signals were sampled by a 12 bit multifunction data acquisition module (DAQ) and were fed into a laptop for real time signal processing by LabVIEW. FIG. 7 shows the antennas and the identical transceivers used for the experiments.

Figures 8A, 8B, 8C:
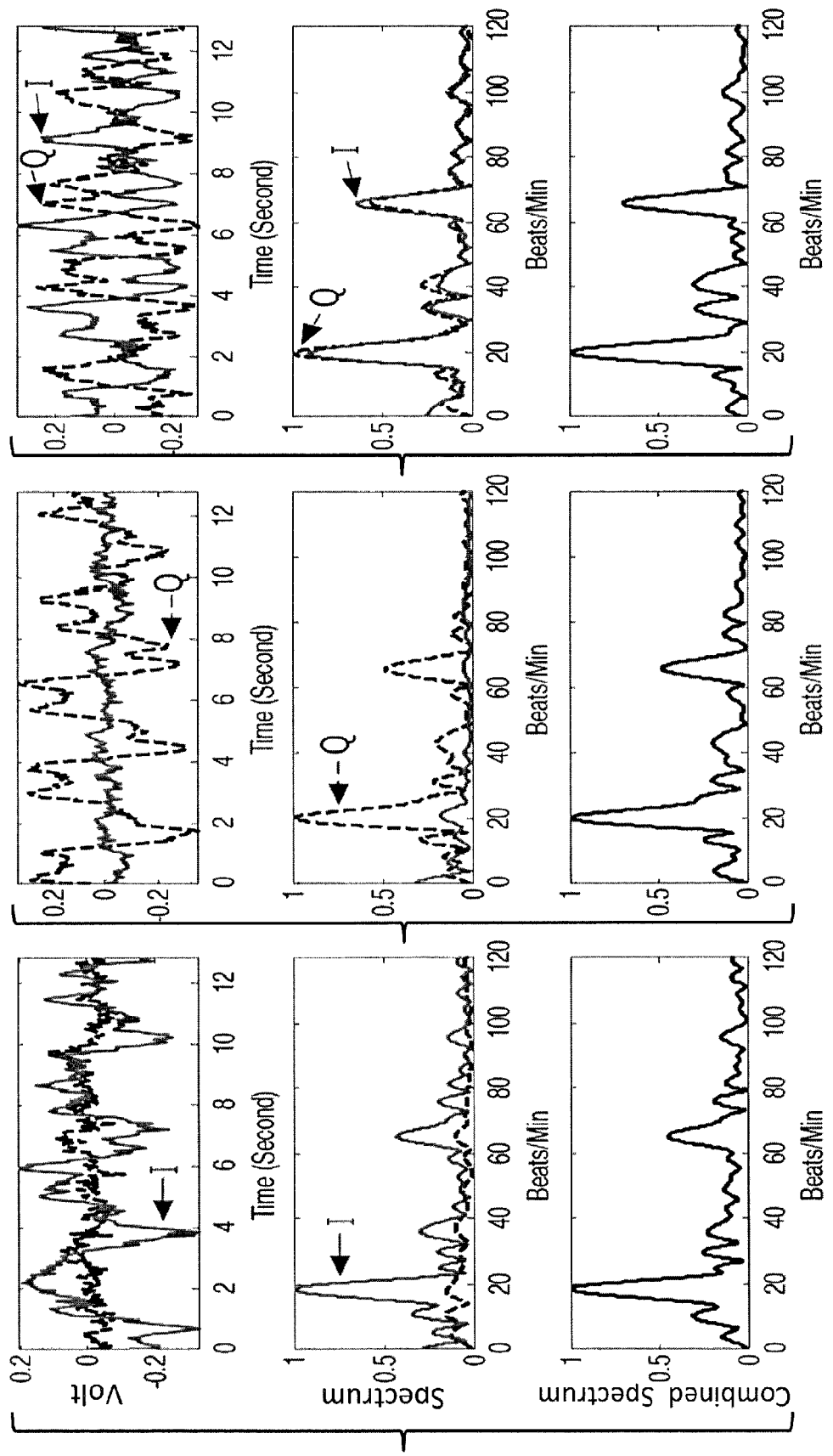
FIGS. 8A-8C show measurement results of complex demodulation, with the time domain signal recorded in the top figures, the I/Q channel spectrum recorded in the middle figures, and the combined spectrum of the complex signal in the bottom figures, where I is at the optimal detection point and Q is at the null detection point in FIG. 8A; where I is at the null detection point and Q is at the optimal detection point in FIG. 8B; and I and Q are both at the point between the optimal and the null detection points in FIG. 8C.

A single transceiver is used to illustrate the complex signal demodulation technique. FIGS. 8A-8C show the measurement results obtained by slightly adjusting the subject-to-antenna distance. FIG. 8A shows results for the case where the I channel was at the optimal detection point while the Q channel was at the null detection point. FIG. 8B shows results for the case where the Q channel was at the optimal while the I channel was at the null detection point. FIG. 8C shows results for the case where both channels are at the midpoint between the null and the optimal. As illustrated in the plots of FIGS. 8A-8C, although the I and the Q channel will change from one state to another (i.e. optimal/null detection) as the distance between the antenna and the subject changes, the reconstructed complex signal has a stable spectrum without the null detection point problem.

Figures 9A, 9B:
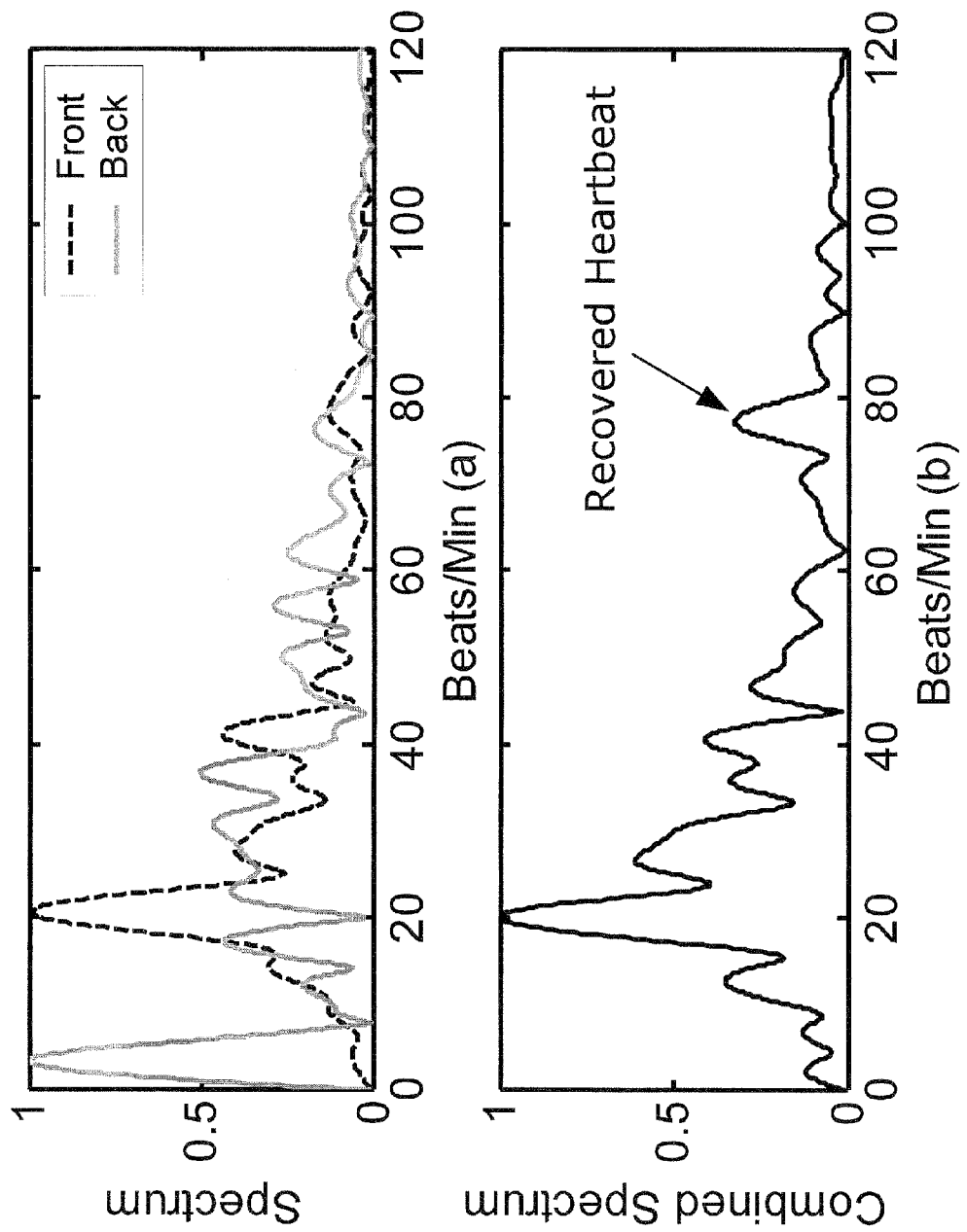
FIGS. 9A-9B show a detected baseband spectrum by the random body movement cancellation technique in accordance with an embodiment of the invention, where

FIGS. 9A-9B show measurement results when two transceivers arranged as illustrated in FIG. 5 are used to verify the random body movement cancellation technique. During experiment, the subject under test was gently changing position in a chair, so that the noise of random body movement was emphasized. Referring to FIG. 9A, since the physiological movement at the back chest wall is weaker than that at the front chest wall, the noise overwhelmed the physiological signal of both the heartbeat and the respiration from the back, and only overwhelmed the heartbeat signal from the front. FIG. 9B shows the result of applying the random body movement cancellation technique according to an embodiment of the present invention to combine the signals detected from the front and the back of the human body. As seen in FIG. 9B, the heartbeat signal was recovered.

Accordingly the complex signal demodulation techniques of embodiments of the present invention are capable of removing the null detection point problem for non-contact vital sign detection. Based on the complex signal demodulation, the random body movement cancellation technique can cancel out random body movement, which is a serious problem for non-contact vital sign detection.

The subject techniques can be implemented in hardware or software. When the techniques are implemented in software, costs can be significantly reduced.

Embodiments of the present invention can be utilized in, for example, healthcare monitoring systems, biomedical sensors, lie-detection systems, military personal radar carried by soldiers for behind-the-wall sensing, and security systems. All of the above are non-contact and can be made portable.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method for recovering a detected signal in non-contact vibration detection, comprising:
    reconstructing a complex signal from an I channel and a Q channel for a received reflected signal to create a reconstructed complex signal;
    applying a Fourier transform to the reconstructed complex signal to obtain a detected spectrum;
    extracting phase angle information of the reconstructed complex signal from the detected spectrum; and
    obtaining original vibration information by analyzing the phase angle information,
    wherein reconstructing the complex signal from the I channel and the Q channel is performed using the following relation:

$$S(t) = I(t) + j \cdot Q(t) = e^{j\left[\frac{4\pi x_h(t)}{\lambda} + \frac{4\pi x_r(t)}{\lambda} + \varphi\right]}$$
$$= DC_I + j \cdot DC_Q + 2j[C_{10}\sin(\omega_y t) + C_{01}\sin(\omega_h t) + \ldots] \cdot e^{j\varphi} +$$
$$2[C_{20}\cos(2\omega_y t) + C_{02}\cos(2\omega_h t) + \ldots] \cdot e^{j\varphi},$$

where $S(t)$ is the reconstructed complex signal, $x_h(t) = m_h \sin(\omega_h t)$ is a first periodic vibration, $x_r(t) = m_r \sin(\omega_r t)$ is a second periodic vibration, $\phi$ is a total accumulated residual phase for the reconstructed complex signal, $\lambda$ is a wavelength of the received reflected signal, and $$C_{ij} = J_i\left(\frac{4\pi m_r}{\lambda}\right) J_j\left(\frac{4\pi m_h}{\lambda}\right),$$

where $J_i$ is a Bessel function of the first kind and $J_j$ is a Bessel function of the first kind, where $$DC_I = J_0\left(\frac{4\pi m_r}{\lambda}\right) \cdot J_0\left(\frac{4\pi m_h}{\lambda}\right) \cdot \cos\phi \text{ and}$$
$$DC_Q = J_0\left(\frac{4\pi m_r}{\lambda}\right) \cdot J_0\left(\frac{4\pi m_h}{\lambda}\right) \cdot \sin\phi$$

are the DC components of the signals in I and Q channels, respectively,
    wherein reconstructing the complex signal from the I channel and the Q channel for a received reflected signal to create the reconstructed complex signal comprises reconstructing the complex signal from the I channel and the Q channel for a received reflected signal to create the reconstructed complex signal via a non-transitory media storage device having machine-readable instructions stored thereon for reconstructing the complex signal from the I channel and the Q channel for the received reflected signal to create the reconstructed complex signal.

2. The method according to claim 1, wherein obtaining original vibration information comprises obtaining original target movement information.

3. The method according to claim 2, further comprising obtaining vital sign information from the original target movement information.

4. The method according to claim 1,
    wherein extracting phase angle information of the reconstructed complex signal from the detected spectrum comprises calibrating out a DC offset of the detected spectrum.

5. The method according to claim 1,
    wherein the original vibration information comprises a first vibration frequency of the first periodic vibration and a second vibration frequency of the second periodic vibration.

6. A method for recovering a detected signal in non-contact vibration detection, comprising:
    reconstructing a complex signal from an I channel and a Q channel for a received reflected signal to create a reconstructed complex signal;
    applying a Fourier transform to the reconstructed complex signal to obtain a detected spectrum;
    extracting phase angle information of the reconstructed complex signal; and obtaining original vibration information by analyzing the phase angle information, wherein reconstructing the complex signal from the I channel and the Q channel is performed using the following relation:

$$S(t) = I(t) + j \cdot Q(t)$$
$$= e^{j\left[\frac{4\pi x_h(t)}{\lambda} + \frac{4\pi x_r(t)}{\lambda} + \varphi\right]}$$
$$= 2j[C_{10}\sin(\omega_r t) + C_{01}\sin(\omega_h t) + \ldots] \cdot e^{j\varphi} +$$
$$2j[C_{20}\cos(2\omega_r t) + C_{02}\cos(2\omega_h t) + \ldots] \cdot e^{j\varphi},$$

where S(t) is the reconstructed complex signal, $x_h(t) = m_h \sin(\omega_h t)$ is a first periodic vibration, $x_r(t) = m_r \sin(\omega_r t)$ is a second periodic vibration, $\phi$ is a total accumulated residual phase for the reconstructed complex signal, $\lambda$ is a wavelength of the received reflected signal, and $$C_{ij} = J_i\left(\frac{4\pi m_r}{\lambda}\right) J_j\left(\frac{4\pi m_h}{\lambda}\right),$$

where $J_i$ is a Bessel function of the first kind and $J_j$ is a Bessel function of the first kind, $$DC_I = J_0\left(\frac{4\pi m_r}{\lambda}\right) \cdot J_0\left(\frac{4\pi m_h}{\lambda}\right) \cdot \cos\phi \text{ and}$$
$$DC_Q = J_0\left(\frac{4\pi m_r}{\lambda}\right) \cdot J_0\left(\frac{4\pi m_h}{\lambda}\right) \cdot \sin\phi$$

are the DC components of the signals in I and Q channels, respectively, wherein reconstructing the complex signal from the I channel and the Q channel comprises reconstructing the complex signal from the I channel and the Q channel via hardware.

7. The method according to claim 1, wherein applying a Fourier transform to the reconstructed complex signal to obtain a detected spectrum;

extracting phase angle information of the reconstructed complex signal; and obtaining original vibration information by analyzing the phase angle information reconstructing the complex signal from the I channel and the Q channel comprises applying a Fourier transform to the reconstructed complex signal to obtain a detected spectrum;

extracting phase angle information of the reconstructed complex signal; and obtaining original vibration information by analyzing the phase angle information via the non-transitory media storage device, wherein the non-transitory media storage device has machine-readable instructions stored thereon for:

applying a Fourier transform to the reconstructed complex signal to obtain the detected spectrum;

extracting phase angle information of the reconstructed complex signal; and obtaining original vibration information by analyzing the phase angle information.

8. The method according to claim 5, wherein the first periodic vibration is due to heartbeat and the second periodic vibration is due to respiration.

9. The method according to claim 4, wherein calibrating out the DC offset of the detected spectrum comprises subtracting a complex average from every time domain sliding window.

10. The method according to claim 1, wherein extracting the phase angle information of the reconstructed complex signal from the detected spectrum comprises applying the following relation:

$$\text{Phase}[S(t)] = \frac{4\pi x_h(t)}{\lambda} + \frac{4\pi x_r(t)}{\lambda} + \phi,$$

where S(t) is the reconstructed complex signal, $x_h(t)$ is a first periodic vibration, $x_r(t)$ is a second periodic vibration, $\phi$ is a total accumulated residual phase, and $\lambda$ is a wavelength of the reflected signal.

11. The method according to claim 1, further comprising:

transmitting a transmit signal at a target such that the transmit signal is reflected by the target to create a reflected signal; and receiving the reflected signal from the target to create the received reflected signal.

12. The method according to claim 11, wherein the transmit signal has a frequency in a range of 9 kHz-1 terahertz.

13. The method according to claim 11, wherein the transmit signal has a frequency in a range of 1 GHz-30 GHz.

14. The method according to claim 11, wherein the I channel is a real component I of the received reflected signal, wherein the I channel is in-phase with the transmit signal, wherein the Q channel is an imaginary quadrature component Q of the received reflected signal, wherein the Q channel is 90 degrees out of phase with the transmit signal.

15. The method according to claim 1, wherein analyzing the phase angle information comprises determining how fast a phase angle of the reconstructed complex signal changes.

16. The method according to claim 15, wherein a vibration rate of the target is how fast the phase angle of the reconstructed complex signal changes.

17. A method for cancelling random target movement effects in non-contact vibration detection, comprising:

transmitting a first transmit signal from a first position at a target such that the first transmit signal is reflected by the target to create a first reflected signal, wherein the first transmit signal has a first polarization;

transmitting a second transmit signal from a second position at the target such that the second transmit signal is reflected by the target to create a second reflected signal, wherein the second transmit signal has a second polarization, wherein the second position is different than the first position, wherein the second polarization is different than the first polarization;

receiving the first reflected signal to create a first received reflected signal;

receiving the second reflected signal to create a second received reflected signal;

reconstructing a first complex signal from a first I channel and a first Q channel for the first received reflected signal to create a first reconstructed complex signal, and reconstructing a second complex signal from a second I channel and a second Q channel for the second received reflected signal to create a second reconstructed complex signal; and combining the first reconstructed complex signal and the second reconstructed complex signal to produce a combined signal, wherein reconstructing a first complex signal from a first I channel and a first Q channel for a first received reflected signal to create the first reconstructed complex signal and reconstructing a second complex signal from a second I channel and a second Q channel for a second received reflected signal to create the second reconstructed complex signal are performed via a non-transitory media storage device having machine-readable instructions stored thereon for performing reconstructing a first complex signal from a first I channel and a first Q channel for the first received reflected signal to create the first reconstructed complex signal and reconstructing a second complex signal from a second I channel and a second Q channel for a second received reflected signal to create the second reconstructed complex signal.

18. The method according to claim 17, wherein reconstructing the first complex signal from the I channel and the first Q channel for a first received reflected signal to create the first reconstructed complex signal and reconstructing a second complex signal from a second I channel and a second Q channel for a second received reflected signal to create the second reconstructed complex signal are performed using the following relations:

$$S_1(t) = \exp\left\{j\left[\frac{4\pi m_{r1}\sin(\omega_r t)}{\lambda_1} + \frac{4\pi m_{h1}\sin(\omega_h t)}{\lambda_1} - \frac{4\pi vt}{\lambda_1} + \phi_1\right]\right\}$$

$$S_2(t) = \exp\left\{j\left[\frac{4\pi m_{r2}\sin(\omega_r t)}{\lambda_2} + \frac{4\pi m_{h2}\sin(\omega_h t)}{\lambda_2} - \frac{4\pi vt}{\lambda_2} + \phi_2\right]\right\},$$

where $S_1(t)$ is the first reconstructed complex signal, $S_2(t)$ is the second reconstructed complex signal, $m_h \sin(\omega_h t)$ is a first periodic vibration, $m_r \sin(\omega_r t)$ is a second periodic vibration, $\phi_1$ is a total accumulated residual phase for the first reconstructed complex signal, $\phi_2$ is a total accumulated residual phase for the second reconstructed complex signal, $\lambda_1$ is a first wavelength of the first reconstructed complex signal, $\lambda_2$ is a second wavelength of the second reconstructed complex signal, and v is a random variable representing a velocity of random target movement.

19. A method for cancelling random body movement effects in non-contact vibration detection, comprising:
transmitting a first transmit signal from a first position at a target such that the first transmit signal is reflected by the target to create a first reflected signal, wherein the first transmit signal has a first polarization;
transmitting a second transmit signal from a second position at the target such that the second transmit signal is reflected by the target to create a second reflected signal, wherein the second transmit signal has a second polarization, wherein the second position is different than the first position, wherein the second polarization is different than the first polarization;
receiving the first reflected signal to create a first received reflected signal;
receiving the second reflected signal to create a second received reflected signal;
reconstructing a first complex signal from a first I channel and a first Q channel for the first reflected signal and reconstructing a second reconstructed complex signal from a second I channel and a second Q channel for the second received reflected signal; and
combining the first reconstructed complex signal and the second reconstructed complex signal to produce a combined signal, wherein reconstructing a first complex signal from a first I channel and a first Q channel for the first reflected signal and reconstructing a second reconstructed complex signal from a second I channel and a second Q channel for the second received reflected signal are performed via hardware.

20. The method according to claim 17, wherein combining the first reconstructed complex signal and the second reconstructed complex signal to produce a combined signal are performed via a non-transitory media storage device having machine-readable instructions stored thereon for performing combining the first reconstructed complex signal and the second reconstructed complex signal to produce a combined signal.

21. The method according to claim 18, wherein) $\lambda_1$ and $\lambda_2$ are within 0.0001% of each other.

22. The method according to claim 18, wherein the first periodic vibration is due to a heart beating and the second periodic vibration is due to respiration.

23. The method according to claim 17, wherein combining the first reconstructed complex signal and the second reconstructed complex signal to produce the combined signal comprises performing a convolution and frequency shift in the frequency domain.

24. The method according to claim 23, wherein combining the first reconstructed complex signal and the second reconstructed complex signal to produce the combined signal comprises applying the following relation:

$$B(t) = S_1(t) \cdot S_2(t)$$

$$= \exp\left\{j\left[4\pi\left(\frac{m_{r1}}{\lambda_1} + \frac{m_{r2}}{\lambda_2}\right)\sin(\omega_r t) + 4\pi\left(\frac{m_{h1}}{\lambda_1} + \frac{m_{h2}}{\lambda_2}\right)\sin(\omega_h t) - \left(\frac{1}{\lambda_1} - \frac{1}{\lambda_2}\right)4\pi vt + \phi_1 + \phi_2\right]\right\}$$

where $S_1(t)$ is the first reconstructed complex signal, $S_2(t)$ is the second reconstructed complex signal $m_h \sin(\omega_h t)$ is a first periodic vibration, $m_r \sin(\omega_r t)$ is a second periodic vibration, $\phi_1+\phi_2$, is the total accumulated residual phase of the combined signal $\lambda_1$ is a first wavelength of the first received reflected signal, and $\lambda_2$ is a second wavelength of the second received reflected signal.

25. The method according to claim 24, wherein the first periodic vibration is due to a heart beating and the second periodic vibration is due to respiration.

26. The method according to claim 24, wherein the combined signal is approximated to:

$$B(t) \approx \exp\left\{j\left[\frac{4\pi(m_{r1} + m_{r2})}{\lambda}\sin(\omega_r t) + \frac{4\pi(m_{h1} + m_{h2})}{\lambda}\sin(\omega_h t) + \phi_1 + \phi_2\right]\right\},$$

where $\lambda$ is a wavelength near the first wavelength of the first received reflected signal.

27. The method according to claim 17, further comprising:
applying a Fourier transform to the combined signal to obtain a detected spectrum;
extracting phase angle information of the combined signal; and
obtaining original target movement information by analyzing the phase angle information.

28. The method according to claim 27, further comprising:
calibrating out a DC offset of the detected spectrum.

29. The method according to claim 18, wherein $\lambda_1$ and $\lambda_2$ are within 0.0001% of each other.

30. The method according to claim 17, wherein the second polarization is orthogonal to the first polarization.

31. The method according to claim 17, wherein the first position is in front of the target and the second position is in back of the target.

* * * * *